United States Patent [19]

Malmin

[11] Patent Number: 5,203,697
[45] Date of Patent: Apr. 20, 1993

[54] DENTAL IRRIGATING AND ASPIRATION SYSTEM

[76] Inventor: Oscar Malmin, 3621 Federal Way, Boise, Id. 83705

[21] Appl. No.: 705,714

[22] Filed: May 23, 1991

[51] Int. Cl.⁵ .............................................. A61G 1/10
[52] U.S. Cl. ...................................... 433/81; 433/224
[58] Field of Search ............... 433/81, 224, 80, 215, 433/91, 116, 102

[56] References Cited

U.S. PATENT DOCUMENTS

| | | | |
|---|---|---|---|
| 1,447,020 | 2/1923 | Grunberg | 433/91 |
| 3,816,921 | 6/1974 | Malmin | 433/81 |
| 3,962,790 | 6/1976 | Riitano et al. | 433/81 |
| 4,215,476 | 8/1980 | Armstrong | 433/80 |
| 4,276,880 | 7/1981 | Malmin | 433/80 |

FOREIGN PATENT DOCUMENTS 2616652 12/1988 France ............................... 433/224

Primary Examiner—John J. Wilson
Attorney, Agent, or Firm—Reese Taylor

[57] ABSTRACT

A dental irrigating and aspirating instrument utilizes a cannula with a reduced diameter extended member shaped to occlude the apical foramen while conducting irrigating fluid into the apical terminations of root canal preparations. The extended member also serves to occlude the apical foramen while conducting fluid and debris out of the apical regions during aspiration. The extended member can be shaped with a cutting surface to prepare a base for the root canal preparation and root canal filling. Use and fabrication of the instrument for irrigation and aspiration of the fullest depths of the gingival sulci and periodontal pockets in periodontic practice is also described. A handpiece is described that retains the instrument allowing manipulation of the instrument and control of fluids to and from the instrument.

18 Claims, 6 Drawing Sheets

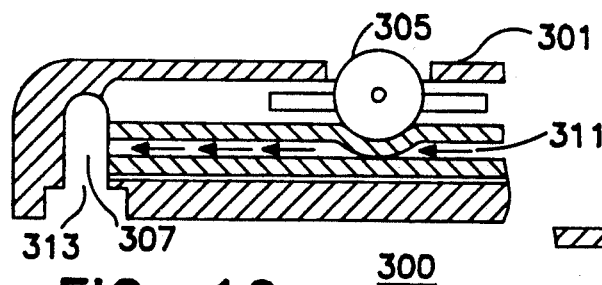
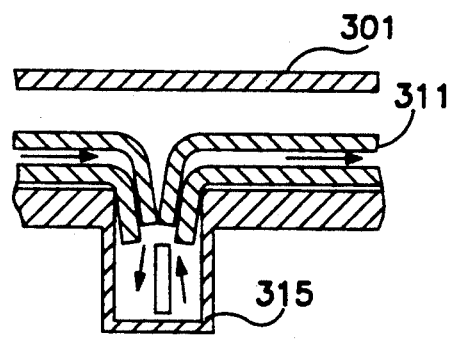
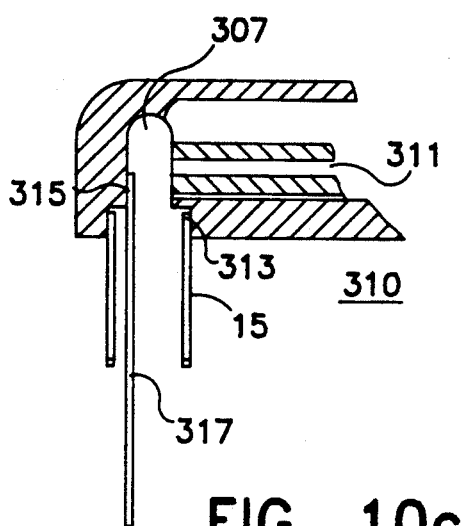
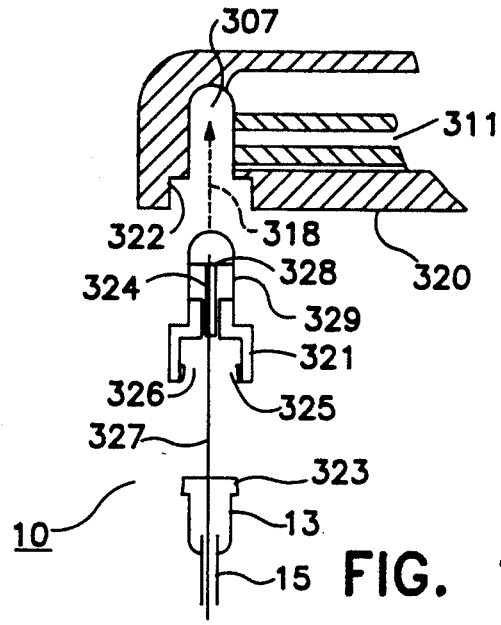
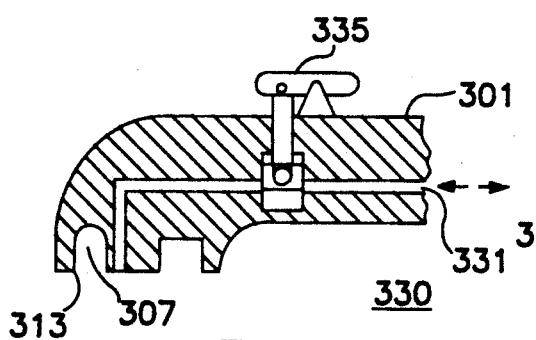
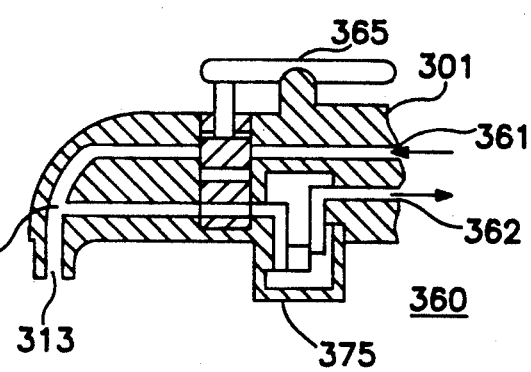

DENTAL IRRIGATING AND ASPIRATION SYSTEM

TECHNICAL FIELD

The present invention relates to endodontics, specifically to root canal therapy and, more particularly, to an instrument for in irrigating and aspirating irrigating fluid and debris from the apical foramen portion of a tooth root canal; and further to periodontics, and more particularly to an instrument for use in irrigating and aspirating irrigating solution and debris from the sulci and periodontal pockets. The present invention can be generally employed for medical, veterinary medicine, industrial and crafts applications.

BACKGROUND ART

In the practice of Dentistry it is common to use a jet of fluid to irrigate or wash an operational area, followed by removal of the fluid and entrained debris by aspirating with a strong vacuum. This practice is suitable for cleaning durable areas such as tooth surfaces but must be moderated when cleaning within confined spaced such as in root canals or endodontic treatment, or around delicate tissues such as around the tooth under the gums or periodontal treatment.

The irrigation of root canal preparations is complicated by the opening ("apical foramen") in the tip of the root(s) through which enter the structures that sustain the pulpal tissues. The apical third (root tip third) of the root canal systems are extremely complicated with an infinite variety of branching much like the delta system of rivers, or the branching of trees from the trunk. Another complication that has been established is that the proper cleansing and sealing of the apical third of root canal systems is the primary criterion for success of the endodontic therapy and the perpetuation and function of the tooth receiving the endodontic therapy.

In the endodontic treatment of root canal systems, it has been clinically established that the root canal systems must be cleansed as thoroughly as possible during the preparation of the primary root canal(s) for filling. It has also been demonstrated that the root canal preparation instruments do not, of themselves, reasonably thoroughly cleanse the primary root canal(s), and that it is not only desirable, but essential, that the root canal preparations be thoroughly irrigated with various chemical solutions designed to remove any remaining pulpal tissues, bacteria, toxins and debris resulting from the action of the root canal preparation instruments of the dentinal wall of the root canal preparation.

If, during the course of preparing the root canal system, preparation instruments are thrust through the apical foramen or, similarly, if irrigating solutions and debris are extruded through the apical foramen, then the periapical tissues surrounding the apical foramen and root of the tooth become inflamed and/or infected which can create intense pain for the patient and may require surgical intervention, or the loss of the tooth.

Thus a primary requirement for endodontic irrigation is to provide blocking or occluding of the apical foramen to prevent the extrusion of debris, irritants or other contaminants from the root canal into the periapical tissues during irrigation.

A tooth can be thought of as a bottle with a narrow neck, turned upside down in the jawbone. The root canal system in a tooth occupies a space very much like the neck of such a bottle. The most critical area of a root canal preparation in endodontics is the apical three to five millimeters of the root tip, i.e., the neck of the bottle in this simile.

The most difficult area to prepare and cleanse in root canal therapy is the apical end of the canal, not only due to its small diameter, but because of the curvature of roots which can be pronounced in some teeth, In addition, the mechanical limitations of most instruments presently available to prepare the root canal system actually work against the precise preparation of the apical third of the root. Consequently, the apical portion is almost invariably the least clean area of the root canal preparation, and most root canals contain debris in the apical third of the root. The cleanlines and seal of the apical third is the most important determinant of the success of root canal treatment.

The present most commonly employed devices for root canal irrigation are blunt hypodermic needles, or blunt hypodermic needles in which half of the cannula wall has been removed for a distance of 4 or 5 millimeters from the tip. Not only are such devices limited by their external diameter, but such devices have no provisions, whatever, to permit them to be placed in the apical termination of the root canal preparation to shield, or close off the apical foramen to avoid forcing irrigating solution and debris into the surrounding periapical tissues. Consequently, these devices typically cannot be placed any further into the root canal preparation than the middle third and the irrigating stream pressure must be drastically reduced to avoid extrusion through the apical foramen. Additionally, the head of the irrigating stream tends to force debris into the apical third. The result is that these devices fail to reasonably and thoroughly irrigate and cleanse the apical third of root canal preparations.

The failure of prior art root canal preparation instruments to reasonably and thoroughly clean the critical apical third of root canal preparations, coupled with the inability of present irrigating delivery devices to be placed in the apical termination of fine or tortuous root canal systems, often results in the sealing of debris laden apical thirds of root canal preparations with a termination diameter of 0.30 millimeters or less. Thus, root canal irrigation is the most neglected phase of endodontic therapy, especially in fine, tortuous root canals.

Upon completion of the irrigating process, irrigating solutions, which remain in the root canal preparations(s), must be removed, since it is desirable that the root canal preparation be as dry as possible prior to sealing and filling the root canal preparation.

Presently used are ordinary hypodermic needles and syringes that cannot be efficiently placed in the apical third, or rolled, tapered paper cones that required tedious, numerous placement and removal to absorb the moisture, and which may act to tamp debris into the critical apical third of the root canal preparation.

Again, the apical foramen must be shielded to avoid tamping debris through the apical foramen (as with the paper cones) and creating irritation, inflammation and/or infection in the periapical supportive tissues or suctioning bacteria or tissue elements through the apical foramen into the critical apical third, thereby possibly contaminating the critical apical third region.

Efforts to enhance the irrigation and aspiration of the irrigating solution from tooth surfaces, cavities and especially roots are evident in the prior art. U.S. Pat. No. 3,624,907 (Brass et al.) discloses a device for irrigating and simultaneously aspirating the irrigation fluid from tooth cavities, including root canals. Brass discloses a small diameter tube which is inserted into the tooth and a handle connected to the tube which switches the handle end of the tube alternately to either a supply of irrigating liquid or a source of vacuum for aspirating the liquid out of the tooth cavity. The tube disclosed by Brass necessarily must be of a small external diameter in order to reach into the tooth cavity. This small external diameter limits the opening inner diameter of the tube through which the liquid and any debris from the therapy is withdrawn from the cavity. The external diameter of the tube limits the ability of the practitioner to insert the tube into the apical third of the canal. The smaller diameter of the tube opening limits the size of the debris particle which may be withdrawn through the tube. Brass does not suggest how larger debris particles may be withdrawn nor how the instrument may be inserted into the apical third of the canal.

U.S. Pat. No. 3,749,090 (Stewart) discloses an instrument for alternatively delivering fluid to a surgical site and removing fluids from the site by vacuum aspiration. Stewart discloses a handle attached to removable hollow tubes which may be sterilized for use in aseptic procedures. Stewart teaches that such an instrument is suitable for surgical procedures but does not suggest how it may be adapted for use in extremely small surgical procedures such as root canal therapy.

U.S. Pat No. 3,164,153 (Zorzi) discloses an instrument adapted for delivering a liquid to an oral operating site and alternatively aspirating liquids from the site through tubes by use of a compressed air system commonly available to dental practitioners. The needle-like tubes described by Zorzi have an inner opening diameter determined by the exterior dimension of the needle and the wall thickness thereof. Zorzi does not suggest how the exterior dimension may be reduced to readily reach into the apical region of a tooth root canal nor how the inner opening diameter may be increased to allow the passage of debris particles from the canal.

U.S. Pat. No. 4,340,365 (Pisanu) discloses a larger instrument for cleaning work areas such as the oral cavity. Pisanu increases the opening of the aspirating tube by placing it circumferentially around the outside of a smaller inner tube which serves to direct the cleaning liquid into the operating site. The instrument disclosed by Pisanu may be made large enough to aspirate larger debris particles but is then too large to be inserted into the tooth root canal. The smaller liquid delivery tube may force a jet of liquid into the apical portion of the canal which may carry with it debris particles which may become lodged in the small passages of the canal, preventing their aspiration by the larger tube.

U.S. Pat. No. 4,215,476 (Armstrong) discloses how an instrument for delivering and aspirating liquids may be joined through a suitable handpiece to a source of several fluid reservoirs. Armstrong utilizes concentric tubes to deliver the fluid and aspirate it from the operation site as is customary in the present art. Armstrong does not, however, address the miniaturization of the instrument in order to reach the innermost portion of small operating areas such as the apical third of a tooth root canal preparation.

Each of the above described instruments for lavage and aspiration in the field of endodontics suffer from the same limitations due to size of the tip portion to be inserted into the tooth cavity. As the external dimension is reduced to allow insertion of the instrument further into a root canal, the inner opening dimension is reduced to a point where the opening is too small to allow the passage of debris particles.

Perhaps the safest and most effective device of this kind is that of U.S. Pat. No. 4,276,880, in which the device has a closed, rounded tip designed to close off the apical foramen with a precise side-window design, all as integral in one cannula that effectively disperses the impact force of the fluid irrigating stream, while creating a highly turbulent cleansing action of the irrigating solution. This device adequately answers the irrigating requirements for root canal preparations that have a root canal preparation termination diameter of 0.30 millimeters, or larger. However, there are many root canal preparations that may vary in the root canal termination diameter from 0.10-0.25 millimeters, in which this device cannot be seated due to the limitations of the external diameter of the device. The device could be produced in a smaller external diameter except for the fact that the present smallest external diameter of manufactured metal cannula tubing is approaching the manufacturing limits of ensuring that a patent internal channel (lumen) is maintained in the metal cannula tubing. Manufacturing capabilities, presently, do not make it possible to produce realistic and economically feasible cannula tubing of external diameter less than 0.30 millimeters having a realistic internal diameter of the lumen, nor can this be overcome by the presently available extrusion or molding processes for hollow plastic tubing.

In periodontal irrigation it is necessary to avoid injury to the delicate epithelial and connective tissue attachments joining the tooth root to the bone when a cannula or tube carrying the irrigating fluid is placed on the bottom of the sulcus or the periodontal pocket. Thus, as the means of obstructing the apical foramen assumes a broad coverage to assure maximum sealing of the foramen by the intraprobe cannulas, in a similar manner, the delicate attachments of the periodontal tissues connecting the tooth and bone require a comparatively broad contact surface to distribute the force of the irrigating fluid and instrument contact in order to minimize the potential of penetration of the epithelial and connective tissue attachments by the irrigating/aspirating intraprobe cannulas.

Although the hydraulic principles are comparable in endodontic and periodontal subgingival irrigation, several problems are inherently unique to periodontal subgingival irrigation. First, the delicate epithelial and connective tissue attachments must be spared from tearing or laceration by any subgingival irrigating device, and, secondly, the impact force of the irrigating stream must be sufficiently dispersed so as not to impact bacteria, toxins, calculus or other debris into the surrounding soft tissues. Further, the impact force of the irrigating stream must not create a stripping or tearing of the delicate attachment tissues.

Prior art devices used for subgingival irrigation comprise various forms of open-ended cannulas (such as blunted hypodermic needles) used with hand syringes, or oral irrigation devices, and various forms of tapered tips attached to oral irrigating devices.

All of these have serious limitations both as to tearing and lacerating tissues by the edges or tips of the devices, and because the narrowing of the irrigating passages concentrates the impact force of the irrigating stream finally emerging from the open end of the devices in a manner potentially comparable to the effects of a miniature "water cannon", which can blast away the delicate tissue attachments and impact bacteria, toxins, calculus and other debris into the vulnerable connective-supportive tissues.

The device disclosed by U.S. Pat. No. 4,276,880, discussed above, includes a smooth, rounded, closed-end which prevents tearing or laceration of the tissues by the tip or end of the device. A side-window design disperses the impact of the fluid stream into a gentle, "shower-like", highly turbulent cleansing flow. The limitation of this device is that it is expensive to manufacture, requires a manufacturing capability of the highest tolerances and cannot be utilized in root canal preparations of the smaller diameters.

DISCLOSURE OF THE INVENTION

An objective of the present invention is to provide a preformed device that will enable the operator to irrigate the full extent of the root canal preparation in fine and tortuous root canal preparations that cannot be irrigated by means of the presently available devices.

A further objective of the present invention is to protect the apical foramen and prevent contamination through the inadvertent extrusion of irrigating solutions and debris through the apical foramen into the surrounding periapical tissues during the irrigating phase of root canal preparations that might lead to inflammation and infection creating acute pain for the patient and possibly leading to the necessity of surgical intervention or the loss of the tooth.

Another objective of the present invention is to employ a preformed, bendable cannula and apical foramen (sulcus) guard that will be simple, safe, effective and easily employed by any operator.

An additional objective of the present invention is to employ a preformed cannula and apical foramen (sulcus) guard device that is simple and economical of manufacture.

Yet another objective of the present invention is to permit the precise placement of the invention in the fullest depths of root canal preparations and gingival sulci and periodontal pockets in a reliable, consistent, easy and efficient manner.

Among the principal objects of this invention are to provide intraradicular irrigation devices of safe, highly efficient, effective and diversified clinical usage that are uncomplicated in design and manufacture and particularly well adapted for the proposed safe and effective irrigation and aspiration of root canals of any diameters preparation.

Other principal objects of this invention are to provide subgingival irrigation devices of safe, highly efficient, effective and diversified clinical usage that are uncomplicated in design and manufacture and particularly well adapted for the proposed safe and effective subgingival irrigation and aspiration necessary to control and prevent various periodontal diseases.

These and other objectives are achieved in accordance with the present invention, wherein a dental irrigating and aspirating instrument is provided utilizing a shaped, elongated probe-like, extended member having a shaped distal end utilized with an open-ended cannula joined to an engagement means which provides an irrigating fluid or a source of suction.

The present invention capitalizes on the shape of the final termination of the root canal preparation, regardless of the form of preparation instrument used, in order to irrigate and aspirate effectively from all reaches of the root canal. The present invention provides a range of selectable probes of various dimensions suitable for reaching the apical end of the canal. The probe distal end is shaped in a manner to conform to the shape of the base or termination of the preparation so as to effectively block the apical foramen or opening from the end of the canal into the jaw bone while leaving space between the shank of the probe and the root canal wall for the passage of the irrigating fluid.

The probe extends beyond the end of a tubular member or cannula a suitable distance to allow the tubular member to be formed with a dimension large enough to accept the debris from the canal preparation. Both the probe and cannula are bendable for convenient access to the root cavities and to provide maximum versatility in root canal preparation. The tubular member is switchably connected to a source of irrigating fluid and a source of vacuum in a manner well known in the art.

In endodontic use, the practitioner inserts a suitably shaped probe tip into the canal, sealing the apical foramen. Irrigating fluid is then introduced into the tubular member and is carried down into the apical end of the canal by surface tension and the wetting forces of the liquid on the exterior of the probe. The irrigating fluid entrains the debris from the canal preparation by capturing the debris by the surface tension of the liquid on the exterior of the probe. When the aspirating vacuum is applied, the entrained debris is moved up the exterior surface of the probe until it is captured by the aspirating tube. Because the debris moves along the exterior of the probe, the larger particles as well as the smaller particles are removed from the canal. The opening of the aspirating tube may be made as large as necessary to allow the passage of the largest debris particles.

In another embodiment of the invention for use in endodontics, the probe is shaped into a cutting surface for preparation of the root canal. This provides the practitioner with a single instrument for both cutting the interior surface of the canal and removing the resulting debris by irrigation and aspiration; thereby eliminating the requirement to switch from a cutting instrument to a cleansing instrument.

In periodontal applications, the practitioner selects a probe having a smooth, shaped distal tip. The suitably shaped tip can be placed without laceration or tissue damage in the base of the sulcus or periodontal pocket. The irrigating fluids are delivered by the instrument in the same manner as described above to the bottom of the sulcus, and gentle aspiration removes the fluid and entrained debris from the pocket without damaging tissues.

The present invention will not only provide the benefits of the device disclosed by U.S. Pat. No. 4,276,880, but will be simpler and less expensive to manufacture. Further, the annular cannula opening of the present invention prevents closure by soft tissues, unlike the limited side-window feature that could be blocked in its entirety by aspirating the soft tissue wall of the sulcus or "pocket", thereby sealing off the window.

BRIEF DESCRIPTION OF THE DRAWING

For fuller understanding of the present invention, reference is made to the accompanying drawing in the following detailed Best Mode of Carrying Out The Invention. In the drawing:

FIG. 1b is an exploded view illustrating the components of the dental instrument shown in FIG. 1a;

FIGS. 1c-1f are cross-sectional views of different forms for the probe and guard of the dental instrument shown in FIG. 1a;

FIGS. 10a and 10b are cross-sectional views illustrating a suitable irrigating handpiece for use with the dental instruments shown in FIG. 1;

FIG. 10c is a cross-sectional view of the handpiece shown in FIG. 10a illustrating another embodiment of the dental instrument according to the principles of the present invention;

FIG. 10d is a cross-sectional view of the handpiece shown in FIG. 10a illustrating another embodiment of the dental instrument according to the principles of the present invention;

FIGS. 11 is a cross-sectional view illustrating another embodiment of a suitable handpiece for use with the dental instrument shown in FIG. 1; and FIG. 12 is a cross-sectional view illustrating a third embodiment of a suitable handpiece for use with the dental instrument shown in FIG. 1.

Figure 1A:
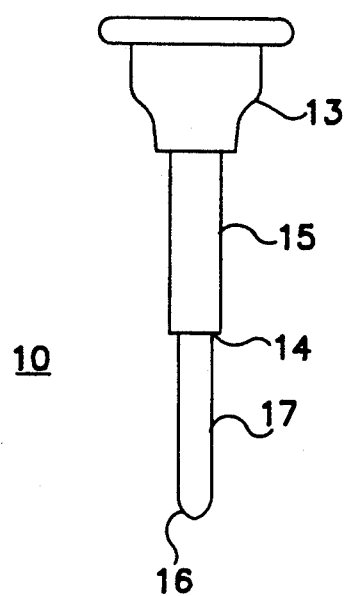
FIG. 1a is a cross-sectional view illustrating a dental irrigating and aspirating instrument constructed in accordance with the principles of the present invention.
Figure 1B:
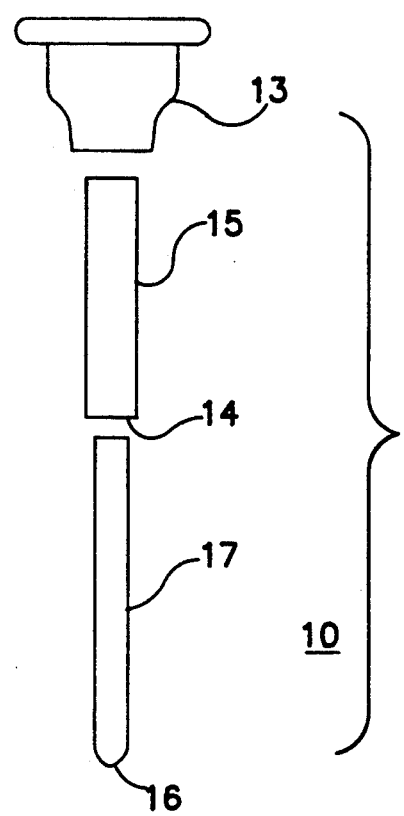
Figure 1C:
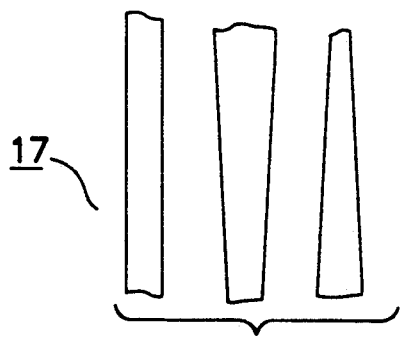
Figure 1D:
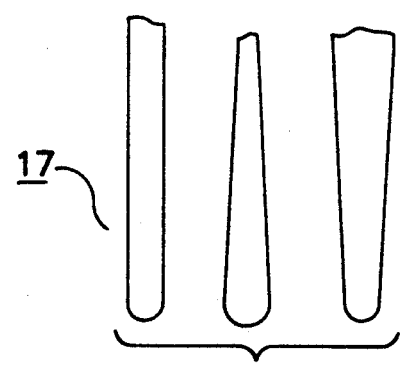
Figure 1E:
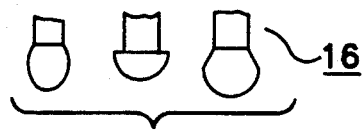
Figure 1F:
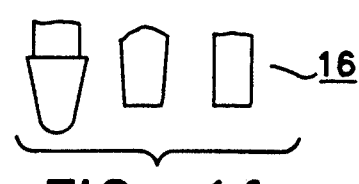

Reference numbers refer to the same or equivalent parts of the present invention throughout the several figures of the drawing.

BEST MODE OF CARRYING OUT THE INVENTION

For purposes of description herein, the terms "upper", "lower", "right", "left", "rear", "front", "vertical", "horizontal", as well as specific dental terms employed, and derivatives thereof shall relate to the invention as oriented in FIGS. 1-12. It is to be understood that the invention may assume various alternative forms, orientations and step sequences except where expressly specific to the contrary. However, for the most ideal usage, the apical guard should be seated fully on the apical termination of the root canal preparation for any sequence of usage in irrigation, and should be seated on the apical termination of the root canal preparation for aspiration of the apical third of the root canal preparation. Similarly, while the instrument can function otherwise, it is preferred that the sulcus guard be placed on the very bottom of the gingival sulcus, or "periodontal pocket", for both the irrigating and aspirating functions.

A root canal instrument has two diameters of importance, the maximum diameter (D2) of the working blade and the blade diameter (D1) involved at the termination of the root canal preparation. In standardized root canal instruments, the distance between the two diameters is 16 millimeters, the taper is 0.02 millimeters per millimeter of length and the difference in diameter is expressed in the equation $D2 = D1 + 0.32$ millimeters. Typically, the smallest diameter root canal instrument used in the final preparation of the termination of a root canal preparation has a D1 diameter of 0.10 millimeters and a D2 diameter of 0.42 millimeters ($D1 + 0.32$ millimeters). The commonly available range of D1 diameters is from 0.10 to 1.50 millimeters.

In order to provide effective irrigation and aspiration, a cannula's external diameter must correlate with the D1 diameter of the final root canal instrument used in the termination of the root canal preparation. This becomes a major clinical problem, when the D1 diameter of the root canal instrument is less than 0.30 millimeters, since the minimum external diameter of the finest cannula commonly available is 0.30 millimeters. Thus, for root canal preparation terminations of a lesser diameter than 0.30 millimeters, it is physically impossible for the finest available cannula to approach the base of the termination of the root canal preparation. That is, the present clinical limitation of such prior art devices, for example, the device described in U.S. Pat. No. 4,276,880, having final termination diameters of less than 0.30 millimeters, makes it physically impossible for the closed end of the cannula to seat on the root canal termination diameter and thus prevent the extrusion of irrigating solution and debris through the apical foramen into the surrounding periapical tissues. The present invention compensates for that deficiency by extending from the cannula a smaller diameter means for closing off the apical foramen prior to irrigation to prevent the extrusion of irrigating solution and debris into the periapical tissues. Such an extension from the cannula comprises an elongated member or probe of cylindrical or variously tapering form having at its distal end a geometrical form, referred to as a guard, that serves to seal off the apical foramen.

It has been found that in the various forms of the invention, such as those shown in FIGS. 1-9, the solution exiting the open end of the irrigating cannulas tends to follow the surface of the probe to its termination at the distal end or guard. Similarly, in the aspirating function, the solution tends to follow the surface of the probe to the irrigating cannulas and thence, to a source of negative (suction) pressure.

Referring now to FIG. 1, an endodontic irrigating and aspirating instrument 10 constructed according to the present invention comprises an elongated member or probe 17 having a shaped distal end 16 and attached at its upper or proximal end to a suitably dimensioned cannula 15. In turn, cannula 15 is attached to a connecting or engagement means 13 at an upper end thereof to employ sources of irrigating solution and suction. Engagement 13 is formed to easily and replaceably connect to a syringe or to a handpiece (as shown in FIGS. 10-12) for controlling the flow of irrigating fluid between the instrument and a dental practitioner's work station. Engagement 13 may be of any form or shape suitable for connecting to a handpiece such as described hereinbelow and as is well known in the art. Throughout the several figures of the drawing, several variations in shape and form of engagement 13 are illustrated.

Cannula 15 is of suitable length to form an easily manipulated instrument and of a suitable interior diameter to accommodate attachment of probe 17 as described hereinbelow and to allow passage of irrigating fluid and aspiration of debris.

Probe 17 comprises a length of material, such as stainless steel, plastic or other suitable material, with an external surface capable of being wetted by the irrigating fluid. For example, probe 17 may comprise a solid rod-like member of sufficient length to reach the varying lengths of a tooth root. Probe 17 is illustrated as an essentially straight shape with a rounded distal end or guard 16. However, probe 17 may be fashioned with any shape or curvature required or desired in order to conform to the root canal and base 22 (as shown in FIG. 2) formed in the canal during the endodontic treatment. FIGS. 1c-1f illustrate several forms for the probe 17 shank and guard 16 which may be employed.

The dimensions as well as the shape and curvature of both the cannula 15 and the probe 17 are determined by the dimensions of the particular tooth or teeth which the instrument 10 will be used with. Since the probe 17 carries the irrigating fluid to the irrigation site (within a tooth root canal cavity or a periodontic pocket), during an irrigation operation it is not necessary that the cannula 15 be inserted into the cavity to be irrigated and, therefore, the size, i.e., the diameter, of the cannula 15 is not limited by the size of the cavity or the access opening in the crown to enter into the root canal of a tooth. However, for efficient aspiration of the irrigating fluid (and entrapped debris) it is desirable to insert the open end of the cannula 15 at least into the upper portion of the cavity. Thus, for a dental instrument 10 which is to be used for both operations, irrigation and aspiration, the diameter of the cannula 15 will be determined by the size of the access opening involved in a particular operation. Both the length and diameter of the probe 17 and the guard 16 are a function of the dimensions of the tooth or teeth to be operated on. For example, a cuspid may be as much as 50 millimeters from its crown to the tip of its root, thus requiring a long, and generally curved, probe 17, while a third molar is much shorter (and broader) and may be only 5-10 millimeters from its crown to the tip of its root thus requiring a much shorter probe 17 while allowing larger diameter instruments to be utilized. Additional, both the cannula 15 and the probe 17 are bendable, having sufficient rigidity to retain a desired curvature, to allow adaptation to a particular tooth or teeth characteristics and to provide versatility and ease of use.

Figures 2A, 2B:
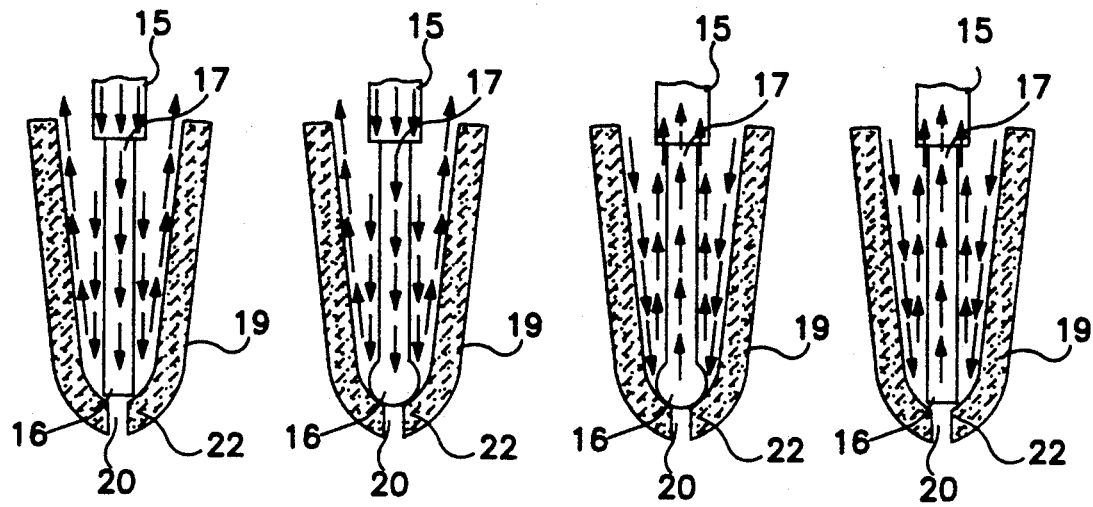
FIGS. 2a and 2aa are cross-sectional views illustrating the general principle of endodontic irrigation in which the distal end of the probe of the dental instrument of FIG. 1 obtunds the apical foramen of a tooth to permit safe irrigation by fluids.
FIGS. 2b and 2bb are cross-sectional views illustrating the general principle of endodontic aspiration of fluids from the apical third of a tooth utilizing the dental instrument of FIG. 1.

Referring now also to FIG. 2(a), the use of dental instrument 10 for irrigation and aspiration of a root canal preparation of tooth 19 is shown. A probe 17 with a distal end 16 having a shape compatible with base 22 is selected by the practitioner. Two possible shapes of guard 16 for sealing the apical foramen 20 are illustrated. Probe 17 is inserted into the canal until distal end 16 contacts base 22, effectively occluding apical foramen 20. The practitioner then provides an irrigating fluid to cannula 15 as described hereinbelow. Probe 17 carries irrigating fluid 18 from cannula 15 into the apical end of the root canal. When the practitioner stops the flow of irrigating fluid and provides an aspirating vacuum, aspiration of the fluid occurs as shown in FIG. 2(b). Irrigating fluid 18 wets the surface of probe 17 and flows under the influence of the aspirating vacuum up probe 17 and out through cannula 15, carrying with it any debris from the root canal preparation.

With continuing reference to FIG. 1, probe 17 is of suitable diameter such that when it is internally mounted in combination with cannula 15, sufficient clearance is provided at the opening in cannula 15 to allow the passage of both irrigating fluid and aspirated fluid and entrapped debris without excessive restriction.

Figures 3A, 3B, 3C:
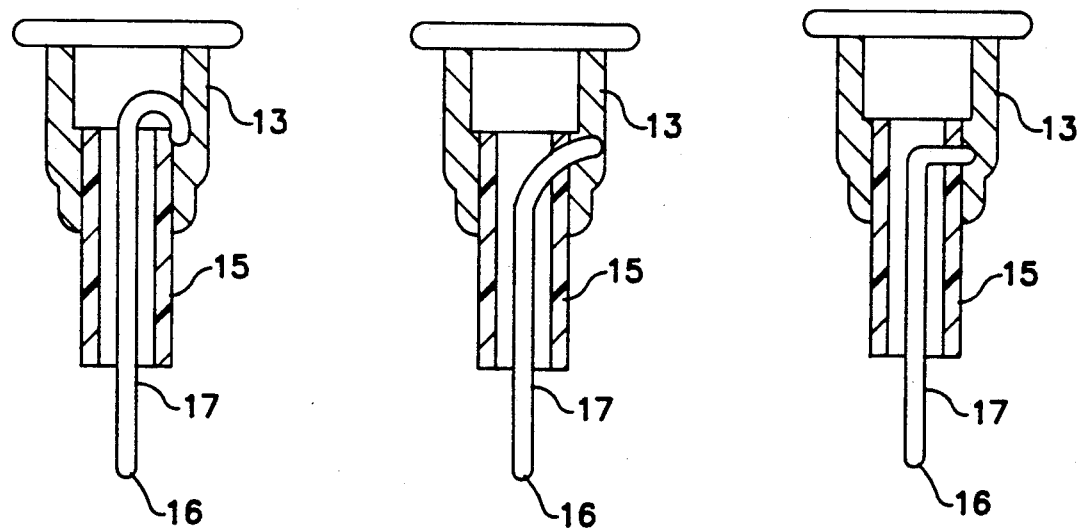
FIGS. 3a, 3b, 3c, 3d, 3dd and 3e are cross-sectional views of alternative embodiments of the dental instruments shown in FIG. 1.
Figure 3D:
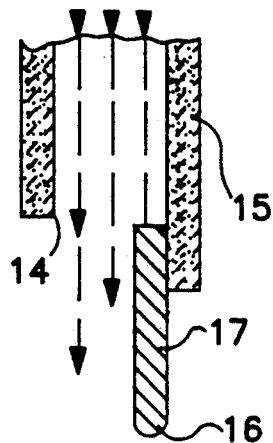
Figure 3D:
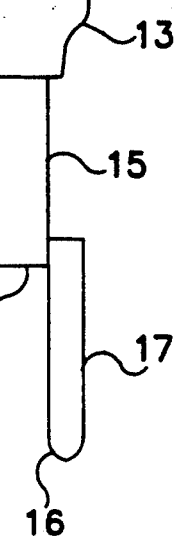
Figure 3E:
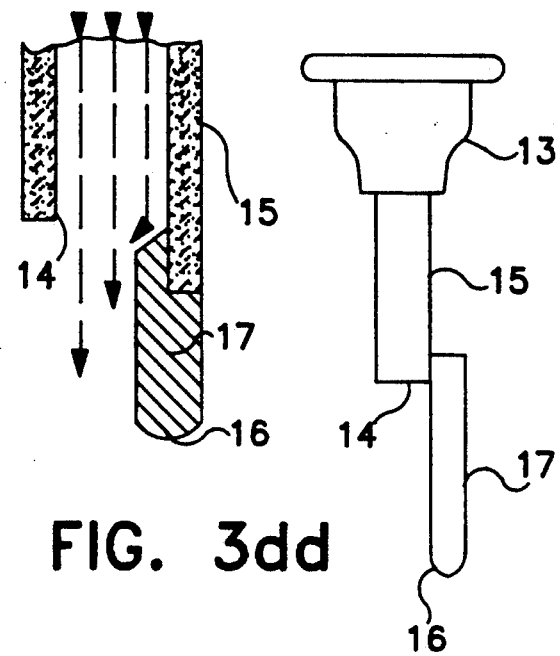

Referring further to FIGS. 3a-3e, alternative mounting arrangements between probe 17 and cannula 15 are shown. As shown, probe 17 may be either internally or externally attached to cannula 15, either by welding, soldering or brazing as is well known in the art. Alternatively, probe 17 may be pressed or crimped into a suitably shaped recess in cannula 15. The choice of attachment method is determined by the materials of which the components are made and ease of manufacturing considerations. In all mounting arrangements it is desirable that the sidewalls of cannula opening 14 be sufficiently close to probe 17 so that the irrigating fluid is most easily and efficiently dispensed and aspirated through opening 14. While it is preferred that the probe 17 be disposed with the cannula 15, either concentric therewith or adjacent a sidewall thereof, the probe 17 can be attached to the exterior sidewall of the cannula 15 (as shown in FIG. 3e) to provide unobstructed entry into the cannula opening 14 for the irrigating fluid and entrapped debris. However, exterior attachment of the probe 17 to a cannula sidewall increases the overall outside diameter of the cannula/probe combination.

With continuing reference to FIG. 3a, the probe 17 at its proximal end may be attached to the interior wall of engagement 13. For example, engagement 13 may be fabricated of molded plastic with the proximal end of probe 17 being seized by the plastic as the plastic solidifies during the molding process. The cannula 15 is then attached to the engagement 13 lower end 11 in a well-known manner with the probe 17 protruding through and extending from cannula 14.

Figure 4:
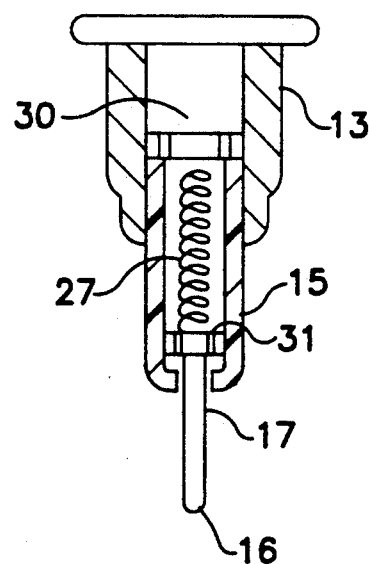
FIG. 4 is a cross-sectional view of the dental instrument shown in FIG. 1 constructed with a probe movably attached to the cannula.

Referring now to FIG. 4, an additional embodiment of instrument 10 is shown. It may be desirable in some applications for probe 17 to be movably attached. This may be especially desirable in endodontics, for example, to maintain the guard 16 in contact with the floor of the root canal preparation. Elongate member or probe 17 is formed with a mounting plate 31 at the upper end thereof suitable for receiving and restraining one end of spring 27. Cannula 15 is formed with one end partially closed to retainably accept probe 17 yet provide sufficient opening for passage of the irrigating fluid and debris when used for aspiration. Spring 27 is compressed between attaching plate 30 and mounting plate 31. Attachment plate 30 and mounting plate 31 include a plurality of apertures formed therein as described hereinbelow to provide passage of the irrigating fluid and debris. Cannula 15, containing spring 27, probe 17 with mounting plate 31 and attachment plate 30, is then pressed into engagement 13 and retained by friction, welding, soldering, brazing or other suitable means.

Figure 5:
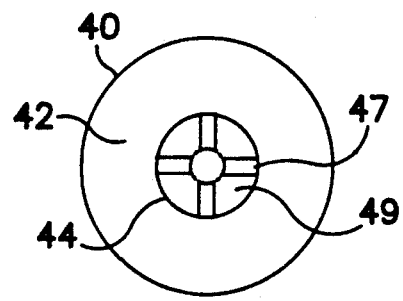
FIG. 5 is a plan view illustrating an alternative form for the probe attaching plates shown in FIG. 4.

Referring now to FIG. 5, one of the many possible forms suitable for attachment plate 30 is shown. Attachment plate 30 may be fabricated of any suitable material which may be sterilized for use. Durable materials such as stainless steel are preferred. Exterior rim 40 is of a suitable dimension to fit the interior diameter of engagement 13. Surface 42 accepts one end of spring 27. Inner area 44 may contain apertures 49 and supporting arms 47 if desirable. Inner area 44 may also be a single aperture.

Figure 6:
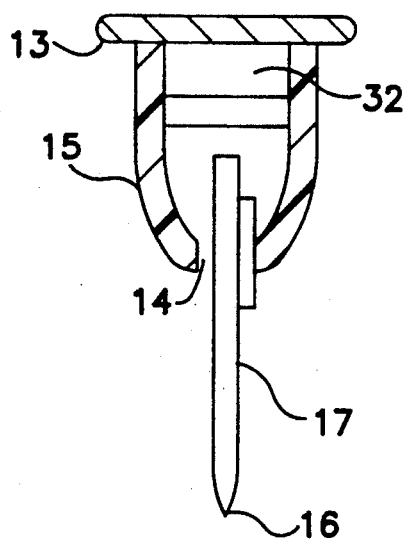
FIG. 6 is a cross-sectional view of the dental instrument shown in FIG. 1 constructed with a filter internally disposed in the cannula.

Referring now to FIG. 6, another embodiment of instrument 10 is shown. It may be desirable in some applications for a filter 32 to be inserted in cannula 15 to trap debris during aspiration. Filter 32 may be of any material which may sterilized before use. Permanent filters made of stainless steel or disposable filters are suitable, for example. Filter 32 may be an integral part of cannula 15 or may be a removable component to allow cleaning.

Figure 7A:
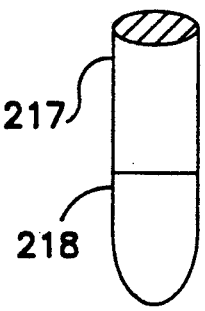
FIGS. 7a, 7b and 7e are perspective views of additional embodiments of the probe of the dental instrument shown in FIG. 1 configured to provide a cutting surface.
Figure 7B:
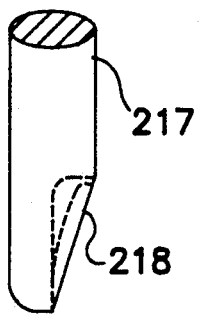
Figure 7C:
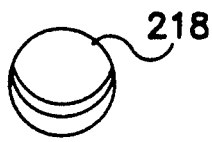
FIGS. 7c, 7d and 7f-7h are end views illustrating alternative shapes for the cutting surface of the probes shown in FIGS. 7a, 7b and 7e.
Figure 7D:
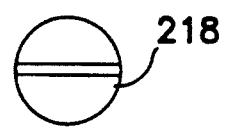
Figure 7E:
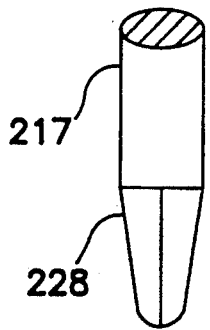
Figure 7F:
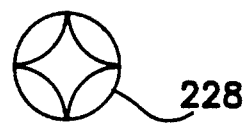
Figure 7G:
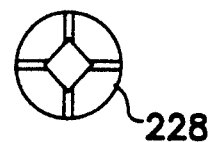
Figure 7H:

Referring now to FIGS. 7a-7h, another embodiment of probe 17 of the dental instrument 10 is shown. Cutting probe 217 is formed with cutting surface 218 in a manner well known in the art. Cutting surface 218 may be curved as shown in FIG. 7c or straight as shown in FIG. 7d. Multiform cutting surface 228 may also be desirable for some applications. Typical multiform cutting surfaces are shown in plan view in FIGS. 7c, 7d, 7f, 7g and 7h. Other shapes as are known in the art are also acceptable.

Figure 8A:
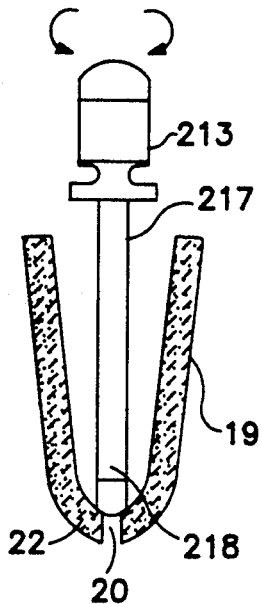
FIG. 8a is a cross-section illustrating of the use of the instrument FIG. 7 in preparing a seat of a root canal preparation.
Figure 8B:
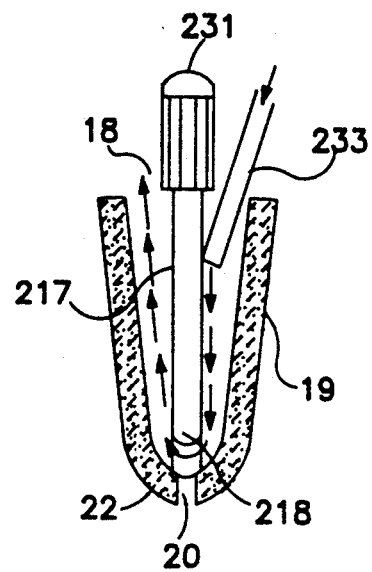
FIGS. 8b and 8c cross-sectional views illustrating an alternate method of irrigation and aspiration with the dental instrument shown in FIG. 8a in accordance with the principles of the present invention.
Figure 8C:
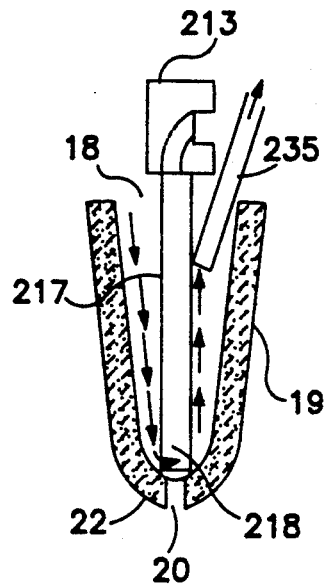

Referring now to FIGS. 8a-8c, the use of the cutting probe 217 shown in FIG. 7 is schematically illustrated. Cutting probe 217 includes a handle 213 to allow manual cutting or milling or may include tang 231 for engagement with the chuck (not shown) of a rotary dental hand piece or power milling apparatus. A practitioner first prepares the root canal base 22 using the cutting feature of cutting surface 218 as shown in FIG. 8a. When a suitable base has been prepared, the practitioner utilizes the irrigating feature of instrument 10 by introducing irrigating fluid 18 into the root canal cavity through a separate irrigation cannula 233 as shown in FIG. 8b. The flow of irrigating fluid 18 is along the surface of the cutting probe 218 to and around the operation site as indicated by arrows in FIG. 8b. The practitioner then utilizes the aspirating feature by aspirating irrigating fluid 18 from the root canal cavity through a separate aspiration cannula 235. The irrigation and aspiration cannulas 233, 235, respectively, may be physically separate cannulas, or may be physically the same cannula selectably coupled to both a source of irrigating fluid and vacuum and being used for both purposes.

Figure 9A:
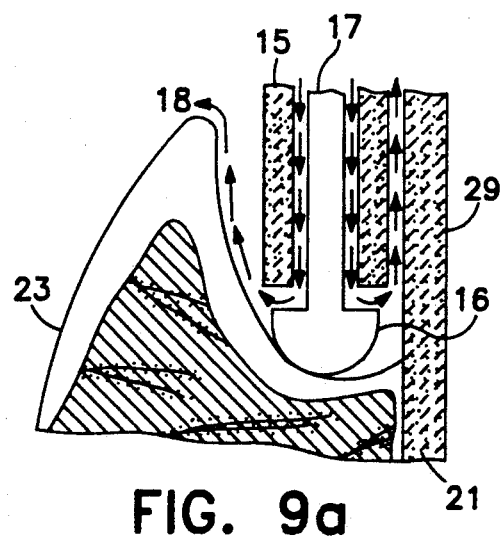
FIGS. 9a and 9b are cross-sectional views illustrating the use of the dental instrument shown in FIG. 1 for irrigation and aspiration, respectively, in periodontic practice.
Figure 9B:
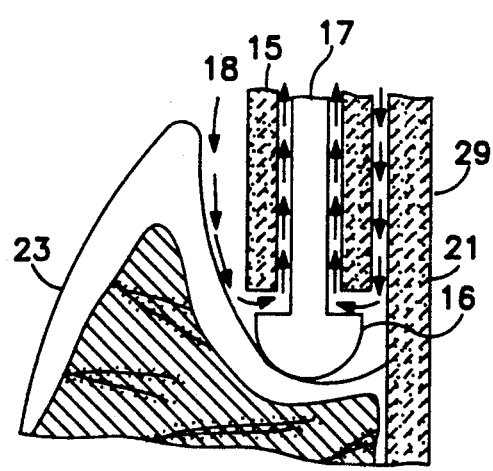

Referring now to FIGS. 9a and 9b, the use of dental instrument 10 in the practice of periodontics is illustrated. Probe 17 is formed with its distal end or guard 16 shaped to provide a broad smooth surface for contacting the connective tissues around the tooth. Probe 17 is illustrated here with bulbous distal end 16 but in practice can be of any suitable form. In the periodontic application, cannula 15 is typically extended further down the length of probe 17 to provide a pathway for aspirating irrigating fluid and entrapped debris from sulcus 21. This forms a pathway by which gentle vacuum can aspirate fluids. In use, probe 17 is inserted into sulcus 21 between the tooth sidewall 29 and gum 23 typically to the bottom of the sulcus or periodontic pocket and irrigating fluid 18 is introduced as shown in FIG. 9a. The general flow of irrigating fluid 18 is indicated by the arrows. As indicated by arrows in FIG. 9b, the irrigating fluid and any detritus is aspirated from sulcus 21 by coupling cannula 15 to a source of vacuum.

Referring now to FIG. 10a and 10b, a handpiece 300 for use with the dental instrument 10 comprises a handle 301 having a head 303 at one end thereof enclosing a cavity 307 and forming an attachment mount 313 for coupling cannula 15 to the handpiece 300. Flexible tubing, or other suitable material, is routed through handpiece 300 to form conduit 311 coupling cavity 307 to the practitioner's workstation sources of irrigating fluid and vacuum in any manner well known in the art. The dental instrument 10 is removably attached or coupled to handpiece 300 and cavity 307 at attachment mount 313 utilizing engagement 13 in a well known manner. The handpiece 300 allows the practitioner to manipulate the dental instrument 10 and to adjust the flow of fluids. Handle 301 is of any shape to allow for a comfortable grip on the handpiece. Conduit 311 conducts irrigating fluids and aspirated materials. Conduit 311 is capable of being selectively compressed to a closed state by any of various compression devices 305, for example an eccentrically attached wheel. Attachment mount 313 is shaped to conform to and accept engagement 13 of instrument 10. FIG. 10b illustrates another embodiment of handpiece 300 utilizing trap 315 connected in line with conduit 311 to capture and retain debris and other entrapped materials from the aspirated fluid.

Referring now to FIG. 10c, a handpiece 310 is constructed generally as described above with reference to FIG. 10a and incorporating elongated member or probe 317 is illustrated. The probe 317 at its proximal or upper end is mounted within and extends from cavity 307. For example, probe 317 may be fixedly attached, as by brazing or other well-known manner, to an interior wall 315 of the cavity 307. Alternatively, probe 317 may be fabricated with an attachment means formed at its proximal end for engagement with attachment mount 313 for removably mounting probe 317 to handpiece 310. Cannula 15 is mounted to handpiece 310 at attachment mount 313, either directly or via engagement 13, with the probe 317 protruding through and extending from cannula 15.

Referring now to FIG. 10d, a handpiece 320 is constructed generally as described above with reference to FIG. 10a for use with another embodiment of dental instrument 10 is illustrated. Extended member 327 comprises an elongated member or probe as described hereinabove which is centrally mounted at its upper or proximal end in coupling 321. Coupling 321 is a generally elongated U-shaped coupling with an opening 326 at its lower end and including a probe attachment structure 328 for mounting probe 327 thereto and passage way 329. As indicated by arrow 318, coupling 321 is inserted into cavity 307 in the handpiece 320 and retained therein by friction fit or other suitable means at attachment mount 322. Passage way 329 is aligned with conduit 311 providing communication between conduit 311 and opening 326 thus coupling opening 326 to a source of irrigating fluid and aspirating vacuum. Cannula 15 via engagement 13 is removably attached to the lower end of coupling 321 by way of cooperating internal and external threads 325, 323, respectively or by other suitable means such as a Luer lock. When assembled, the extension member 327 extends from coupling 321 and through cannula 15. The combination of the handpiece 320, coupling 321, engagement 13 and cannula 15 allows quick assembly and disassembly and provides ease of cleaning and sterilization of components and replacement of the extended member 327.

FIG. 11 illustrates another embodiment of a handpiece. Handpiece 330 is coupled to the practitioner's workstation sources of irrigating fluid and vacuum in any manner well known in the art. As described above with reference to FIG. 10, handpiece 330 remains dental instrument 10 and allows the practitioner to adjust the flow of fluids. Conduit 331 conducts irrigating fluid and aspirated material as controlled by the practitioner. Control is achieved by the use of a valve, such as spring loaded valve 335, or as constructed in a manner well known in the art.

Referring now to FIG. 12, a third embodiment of a handpiece comprising separate conduits 361, 362 for conducting irrigating fluids and aspiration of irrigating fluids, respectively, for use with instrument 10 is shown. Handpiece 360 is connected to the practitioner's workstation sources of irrigating fluid and vacuum in any manner well known in the art. As described above with reference to FIG. 10, handpiece 360 retains dental instrument 10 and allows the practitioner to adjust the flow of fluids. In use, the practitioner alternatively selects between irrigation and aspiration by use of control 365, designed in a manner well known in the art. Handpiece 360 is constructed with trap 375 in aspiration line 362. Trap 375 is constructed in a manner which allows it to be disassembled from handpiece 360 for cleaning as is well known in the art.

Thus, the present invention anticipates the differences in the anatomical and histological requirements between irrigating root canals and subgingival irrigation safely and effectively. Anatomically, the root canal preparation is enclosed on all sides by hard dentin walls, and the only caveat is that the irrigating solution and debris do not exit through the apical foramen into the vulnerable periapical tissues. Whereas, in subgingival irrigation in the sulcus, or a "periodontal pocket" only one wall is hard dentin material (i.e., the wall formed by the side of the tooth) and the remaining walls are soft epithelial or connective tissues, and the requirement in subgingival irrigation is to reduce the impact force of the irrigating stream so as not to impact irrigating solution and debris into the surrounding soft tissues. In addition, unlike in the root canal preparation, the subgingival irrigation device must have no sharp edges or corners that would cut, abrade or lacerate the comparatively delicate soft tissues of the sulcus, or "periodontal pocket". Further, the device must have the capability of diminishing and dispersing the impact force of the irrigating stream to avoid impaction of the irrigating solution and debris into the delicate soft tissues of sulcus, or "periodontal pocket". It has been found that only a limited number of external diameters of irrigating cannulas need be used for subgingival irrigation, generally, in the range of 21-26 gauge cannulas. Because such comparatively large gauges will enter most gingival sulci, then several principal forms of the invention can be used.

While the invention has been described relating to certain dental applications, it is anticipated that the invention can be used for a number of medical and veterinary medicine applications, such as the treatment of various kinds of infected wounds, cysts and other such applications that may require irrigation (lavage), and/or aspiration of fluids. It is also anticipated that the invention can be used in various manufacturing process and assembly operations and in craft and hobby applications. Thus, it should be readily apparent to those of ordinary skill in the art that various changes and modifications in form and details enabling its use in other applications where wetting fluids are applied or removed from close spaces may be made without departing from the spirit and scope of the invention as set forth in the appended claims.

I claim:

1. A dental irrigating and aspirating instrument for use with a source of irrigating fluid and vacuum comprising:

engagement means for attaching the irrigating and aspirating instrument to the source of irrigating fluid and vacuum in non-rotatable relationship therewith;

a cannula, a proximal end thereof being fixedly attached to said engagement means, for conducting said irrigating and aspirated fluid;

an elongated member extending beyond a distal end of said cannula;

a mounting plate slidingly disposed within said cannula, said elongated member, at a proximal end thereof, attached to said mounting plate and extending from said distal end of said cannula, said mounting plate retained by means disposed at said cannula distal end; and bias means disposed within said cannula for exerting a force against said mounting plate urging said elongated member longitudinally outwardly from said cannula distal end.

2. A dental irrigating and aspirating instrument as in claim 1 further comprising an attachment plate attached to said cannula at said proximal end thereof for retaining said bias means within said cannula.

3. A dental irrigating and aspirating instrument for use with a source of irrigating fluid vacuum comprising:

engagement means for attaching the irrigating and aspirating instrument to the source of irrigating fluid and vacuum in non-rotatable relationship therewith;

a cannula, a proximal end thereof being fixedly attached to said engagement means, for conducting said irrigating and aspirated fluid;

an elongated member extending beyond a distal end of said cannula; and said cannula including a filter means disposed within said cannula for filtering said aspirated fluid.

4. A dental irrigating and aspirating instrument for use with a source of irrigating fluid and vacuum comprising:

engagement means for attaching the irrigating and aspirating instrument to the source of irrigating fluid and vacuum in non-rotatable relationship therewith;

a cannula, a proximal end thereof being fixedly attached to said engagement means, for conducting said irrigating and aspirated fluid;

an elongated member extending beyond a distal end of said cannula; and said elongated member including at least one cutting edge formed in the surface thereof.

5. A dental irrigating and aspirating instrument for use with a source of irrigating fluid and vacuum comprising:
   engagement means for attaching the irrigating and aspirating instrument to the source of irrigating fluid and vacuum in non-rotatable relationship therewith;
   a cannula, a proximal end thereof being fixedly attached to said engagement means, for conducting said irrigating and aspirated fluid;
   an elongated member extending beyond a distal end of said cannula;
   a handpiece for retaining said irrigating and aspirating instrument and controlling the flow of irrigating fluid and the application of vacuum thereto, said handpiece comprising:
   handle means for a user to hold and manipulate said irrigating and aspirating instrument;
   connecting means coupled to a rear end of said handle means for connecting said handpiece to a dental workstation source of irrigating fluid and aspirating vacuum;
   mounting means formed at a front end of said handle means for cooperation with said engagement means for removably attaching said irrigating and aspirating instrument to said handle means;
   conduit means for conducting said irrigating fluid and said aspirated fluid to and from, respectively, said irrigating and aspirating instrument, said conduit means attached to said handle means, said conduit means coupled to a source of irrigating fluid and a vacuum source; and
   control means attached to said handle means for controlling the flow of said irrigating and aspirated fluid.

6. A dental irrigating and aspirating instrument as in claim 5 wherein said conduit means includes a trap means for removing solid debris from said aspirated fluid.

7. A dental irrigating and aspirating instrument as in claim 5 wherein said conduit means is formed integrally with said handle means.

8. A dental irrigating and aspirating instrument as in claim 5 wherein said conduit means comprises a single tube selectively coupled to said source of irrigating fluid and said vacuum source.

9. A dental irrigating and aspirating instrument as in claim 5 wherein said conduit means comprises at least two tubes, one tube coupled to said vacuum source and at least one tube coupled to said source of irrigating fluid.

10. A dental irrigating and aspirating instrument as in claim 5 wherein said elongated member at a proximal end thereof is mounted to said mounting means, said elongated member extending from said dental irrigating and aspirating instrument is attached to said handpiece.

11. A dental irrigating and aspirating instrument as in claim 10 wherein said mounting means includes a cavity formed therein, said cavity communicating with said conduit means, said elongated member fixedly attached at said proximal end thereof to an interior side wall of said cavity.

12. A dental irrigating and aspirating instrument as in claim 5 further comprising coupling means, said elongated member at a proximal end thereof attached to said coupling means, said mounting means including a cavity formed therein, said cavity communicating with said conduit means, said coupling means inserted in said cavity and in engagement with said mounting means for removably mounting said elongated member in said cavity.

13. A dental irrigating and aspirating instrument as in claim 12 wherein said engagement means is removably attached to said coupling means.

14. A dental irrigating and aspirating device for use in endodontic and periodontic procedures comprising:
   coupling means for coupling said irrigating and aspirating device to a source of irrigating fluid and vacuum;
   conduit means, said coupling means attached to a first end thereof, said conduit means for conducting irrigating fluid and aspirated fluid;
   an elongated member attached to and extending from a second end of said conduit means, said elongated member being of a lesser diameter than said conduit means; and
   guard means formed at a distal end of said elongated member, said guard means for contacting a surface at an endodontic or periodontic operation site.

15. A dental irrigating and aspirating device as in claim 14 wherein said elongated member comprises an elongated solid member attached to said second end of said conduit means, said irrigating fluid and aspirated fluid and entrapped debris flowing along the surface thereof.

16. A dental irrigating and aspirating device as in claim 15 wherein said guard means is formed integrally with said elongated solid member.

17. A dental irrigating and aspirating device as in claim 16 wherein said guard means is shaped for sealing the apical foramen for use in an endodontic procedure.

18. A dental irrigating and aspirating device as in claim 16 wherein said guard means is shaped for contact in sulcus and periodontal pockets in a periodontic procedure.

* * * * *

UNITED STATES PATENT AND TRADEMARK OFFICE
CERTIFICATE OF CORRECTION

PATENT NO. : 5,203,697
DATED : April 20, 1993
INVENTOR(S) : Oscar Malmin It is certified that error appears in the above-identified patent and that said Letters Patent is hereby corrected as shown below:

In Column 2, line 7, delete "teeth, In" and substitute therefor ---<u>teeth. In</u>---.

In Column 2, line 14, delete "cleanlines" and substitute therefor ---<u>cleanliness</u>---.

In Column 3, lines 45-46, delete "cleasing" and substitute therefor ---<u>cleansing</u>---.

In Column 16, line 2, between the words "said" and "dental" insert the following ---<u>cannula when said</u>---.

Signed and Sealed this

Twenty-fifth Day of January, 1994

Attest:

BRUCE LEHMAN

*Attesting Officer*  *Commissioner of Patents and Trademarks*